United States Patent [19]

Murayama et al.

[11] 3,959,298
[45] May 25, 1976

[54] PROCESS FOR PREPARING TRIACETONAMINE

[75] Inventors: Keisuke Murayama; Syoji Morimura; Takao Yoshioka; Tomoyuki Kurumada, all of Tokyo, Japan

[73] Assignee: Sankyo Company Limited, Tokyo, Japan

[22] Filed: June 21, 1974

[21] Appl. No.: 481,838

[30] Foreign Application Priority Data
June 23, 1973 Japan.............................. 48-70944
May 30, 1974 Japan.............................. 49-61147

[52] U.S. Cl. ............................................ 260/293.89
[51] Int. Cl.² ....................................... C07D 211/74

[58] Field of Search ............................... 260/293.89

[56] References Cited
UNITED STATES PATENTS
3,513,170   5/1970   Murayama et al............... 260/294.7

*Primary Examiner*—G. Thomas Todd
*Attorney, Agent, or Firm*—Toren, McGeady and Stanger

[57] ABSTRACT

A process for preparing triacetonamine characterized in that acetonine is reacted with water in the presence of at least 12.5 mole % based on acetonine of an acid catalyst.

Triacetonamine is used as an intermediate for light stabilizer for synthetic polymers.

46 Claims, No Drawings

PROCESS FOR PREPARING TRIACETONAMINE

The present invention relates to an improved process for preparing triacetonamine in a high yield.

For the preparation of triacetonamine, there have been known (1) a process wherein acetone is reacted with ammonia in the presence of calcium chloride [H. K. Hall; J. A. C. S. 79, 5444 (1957)] and (2) a process wherein phorone prepared from acetone is reacted with ammonia [W. Heintz; Ann. Chemie 203, 336 (1880)]. However, according to process (1) or (2), yield of the product is as low as about 20% based on acetone and side reaction products are formed in a large amount. Thus, processes (1) and (2) are unsuitable for the production of triacetonamine on a commercial scale.

Further, there has been known a process for preparing triacetonamine by reacting acetonine which can be obtained in a high yield from acetone with a Lewis acid such as calcium chloride and water (Japanese Patent Publication No. 12141/1969). However, said process still has some problems to be solved, since yield of the product is at the highest about 60%, by-product of the reaction comprising resinous substances containing calcium chloride or the like is formed in a large amount and the treatment thereof including a prevention of environmental pollution is not easy.

After intensive investigation for the purpose of improving the process for the preparation of triacetonamine from acetonine, the inventors have found a process for obtaining triacetonamine in a higher yield. The process of the invention has the merits that by-products of the reaction are small in amount and that the treatment is easy. The process of the present invention comprises reacting acetonine with water in the presence of at least 12.5 mol. % of an acid catalyst based on the acetonine.

The reaction is performed at temperatures of above −15°C., preferably up to 150°C. Especially good results are obtained by performing the reaction at temperatures of from 0° to 110°C., most preferably at 0° to 65°C.

Optionally the reaction may be performed under pressure.

It is advantageous to perform the reaction in the presence of an organic solvent. In case that as a solvent a ketone other than acetone is used, the reaction temperature should preferably not exceed 40°C. and is therefore conducted optionally in the range of from −15° to +40°C.

As organic solvents, there may be used, for instance, aliphatic or aromatic, optionally halogenated hydrocarbons, e.g., hexane, heptane, cyclohexane, benzene, toluene, xylene, methylene chloride, chloroform, carbon tetrachloride, trichloroethylene or chlorobenzene; ketones, e.g., acetone, methylethyl ketone, or cyclohexanone; substituted or unsubstituted aliphatic mono- or polyfunctional alcohols, e.g., methanol, ethanol, propanol, isopropanol, butanol, octanol, cyclohexanol, benzyl alcohol, ethylene glycol monomethyl ether or glycol; ethers, e.g., dioxane, tetrahydrofuran or diethyl ether; esters, e.g., ethyl acetate; aprotic polar solvents, e.g., dimethylformamide, dimethylacetamide, dimethylsulfoxide, tetramethylurea, hexamethylphosphoric acid amide, sulfolane, acetonitrile or nitromethane as well as mixtures of such solvents.

Especially suitable as solvents are acetone, diacetone alcohol, mesityloxide, phorone, diacetoneamine, triacetonediamine, lower alcohols having from 1 to 4 carbon atoms or ethylene glycol monomethyl ether or mixtures of such solvents.

Especially preferred is the use of methanol or acetone or a mixture of both as solvent.

Acid catalysts which may be used in the process according to the present invention may be mineral acids, carboxylic acids, organic sulfur-oxygen- or organic phosphorus-oxygen acids.

As organic sulfur-oxygen acids preferably sulfonic acids are used.

As the mineral acid, there can be mentioned hydrohalogen acids e.g., hydrochloric, hydrobromic or hydroiodic acid, nitric acid, sulfuric acid and phosphoric acid.

As the carboxylic acid, there can be mentioned monobasic, dibasic and tribasic aliphatic and aromatic carboxylic acids. For instance, there can be employed saturated and undaturated monobasic aliphatic acids having preferably from 1 to 18 carbon atoms, such as formic acid, acetic acid, propionic acid, butyric acid, lauric acid, palmitic acid, stearic acid, acrylic acid and methacrylic acid, halogen-containing carboxylic acids such as chloroacetic, dichloroacetic or trichloroacetic acid and trifluoroacetic acid, saturated and unsaturated dibasic aliphatic carboxylic acids having preferably from 2 to 12 carbon atoms such as malonic acid, succinic acid, adipic acid, sebacic acid, tartaric acid, malic acid, fumaric acid, maleic acid, tribasic aliphatic carboxylic acids such as citric acid, monobasic optionally substituted aromatic carboxylic acids such as benzoic acid, toluic acid and naphthoic acid, dibasic aromatic carboxylic acids such as phthalic acid and terephthalic acid, and tribasic aromatic carboxylic acids such as trimellitic acid.

As organic sulfur-oxygen acids, there may be mentioned alkylsulfuric acids, such as methylsulfuric acid, sulfinic acids, such as benzenesulfinic acids, but especially sulfonic acids.

As the sulfonic acid, there can be mentioned aliphatic and optionally substituted aromatic sulfonic acids such as methanesulfonic acid, benzenesulfonic acid, p-toluenesulfonic acid, naphthalenesulfonic acid and naphthalene-1,5-disulfonic acid.

As organic phosphorus-oxygen acids, there may be mentioned aliphatic or aromatic phosphonic or phosphinic acids, such as methyl-, benzyl- or phenylphosphonic acid or dimethyl- or diethyl-phosphonic acid or diethyl- or benzenephosphinic acid.

Preferably, the acids used according to the invention have pKa-value in water of below 5, most preferably of 1.5 or lower.

Especially preferred examples of such acids are hydrochloric, hydrobromic, hydroiodic, sulfuric, nitric, benzenesulfonic, p-toluenesulfonic, methanesulfonic, dichloroacetic and trichloroacetic acid.

Further there may be used as acid catalysts in the process according to the invention a salt of such an acid with ammonia or a nitrogen-containing organic base.

In addition there may be used as acid catalysts in the process according to the invention mixtures of the above-mentioned acid catalysts.

As the acid of the salt, there can be mentioned the above described mineral acids, carboxylic acids, organic sulfur-oxygen acids or organic phosphorus-oxygen acids. Preferred are carboxylic acids and especially mineral and sulfonic acids.

As the nitrogen-containing organic base of the salt, there may be mentioned aliphatic, alicyclic and aromatic, primary, secondary and tertiary amines, saturated and unsaturated nitrogen-containing heterocyclic bases, urea, thiourea and basic ion-exchange resins.

For intance, there can be employed aliphatic primary amines having preferably from 1 to 18 carbon atoms, such as methylamine, ethylamine, n-butylamine, octylamine, dodecylamine and hexamethylenediamine, aliphatic secondary amines having preferably from 2 to 16 carbon atoms such as dimethylamine, diethylamine, di-n-propylamine and di-isobutylamine, aliphatic tertiary amines such as triethylamine, alicyclic primary amines such as cyclohexylamine, alicyclic secondary amines such as dicyclohexylamine, optionally substituted aromatic primary amines such as aniline, toluidine, naphthylamine and benzidine, aromatic secondary amines such as N-methylaniline and diphenylamine, aromatic tertiary amines such as N,N-diethylaniline, saturated and unsaturated, nitrogen-containing heterocyclic bases such as pyrrolidine piperidine, N-methyl-2-pyrrolidone, pyrazolidine, piperazine, pyridine, picoline, indoline, quinuclidine, morpholine, N-methylmorpholine, 1,4-diazabicyclo[2,2,-2]octane, acetonine and triacetonamine, urea, thiourea, and highly basic and weakly basic ion-exchange resins such as Amberlites IR-45 and IRP-58 (products of Rhome & Haas Co.).

Preferred examples of the salts of ammonia with mineral acids are ammonium halides, e.g., ammonium chloride, ammonium bromide or ammonium iodide, ammonium nitrate and ammonium borate.

Preferred examples of the salts of ammonia with organic acids are ammonium salts of monobasic and dibasic lower aliphatic carboxylic acids and ammonium salts of monobasic aromatic sulfonic acids such as ammonium formate, ammonium acetate, ammonium di- and trichloroacetate, ammonium trifluoroacetate, ammonium malonate, ammonium benzoate and ammonium p-toluenesulfonate.

Preferred examples of the salts of nitrogen-containing organic bases with mineral acids are methylamine hydrochloride, cyclohexylamine hydrochloride, hexamethylenediamine dihydrochloride, aniline hydrochloride, p-nitroaniline hydrochloride, dimethylamine hydrochloride, diphenylamine hydrochloride, diisobutylamine hydrochloride, triethylamine hydrochloride, triethylamine sulfate, 1,4-diazabicyclo[2,2,-2]octane hydrochloride, triacetonamine hydrochloride, triacetonamine sulfate, urea nitrate, thiourea hydrochloride and hydrochloric acid-treated basic ion-exchange resin.

Preferred examples of the salts of nitrogen-containing organic bases with organic acids are cyclohexylamine formate, pyridine formate, pyridine p-toluenesulfonate, di-n-butylamine acetate, di-n-butylamine benzoate, morpholine succinate, morpholine maleate, triethylamine acetate, triethylamine succinate, triethylamine maleate, aniline acetate and triacetonamine p-toluenesulfonate.

Especially preferred nitrogen-containing organic bases forming such salts are triacetonamine, triethylamine urea or thiourea.

Especially advantageous acids for forming such salts are hydrochloric acid, hydrobromic acid, hydroiodic acid, nitric acid, organic sulfonic acid, or halogeno acetic acid.

Especially good results are obtained by using ammonium salts or salts of the above especially preferred nitrogen-containing organic bases with hydrochloric acid, hydrobromic acid, hydroiodic acid, nitric acid, benzene-sulfonic acid, p-toluenesulfonic acid, methanesulfonic acid, dichloroacetic acid or trichloroacetic acid.

A preferred embodiment of the invention is to use the acid which may be used as an acid catalyst in a stoichiometric ratio to acetonine. Therefore, the invention comprises reacting an acid adduct salt of acetonine of formula (I) with water in the presence of an organic solvent to obtain triacetonamine (II) according to the following reaction formula:

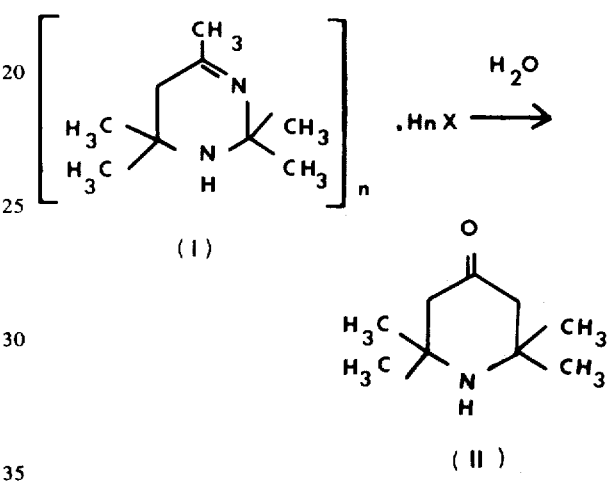

wherein HnX represents an acid selected from the group consisting of mineral acids, carboxylic acids, organic sulfur-oxygen acids or organic phosphorus-oxygen acids and $n$ represents the same number as the ionic valence of acid radical X of the acid.

Monobasic acid adduct salts of acetonine (I) used in the process of the present invention have not yet been known. Moreover, acetonine has been known to be a compound quite unstable to acids, as it is described in J. Chem. Soc. 1947, 1394 and Helv. Chim. Acta. 30, 1114 (1947) that acetonine is decomposed readily into diacetonamine by acids such as oxalic acid and dilute hydrochloric acid. However, the inventors have found that an acid adduct salt of acetonine of formula (I) can be formed substantially quantitatively by reacting acetonine with a stoichiometric amount of an acid in the presence of an organic solvent at a low temperature and that the acid adduct salt per se is relatively stable.

The inventors have further found that triacetonamine can be obtained unexpectedly in a high yield by reacting the acid adduct salt of acetonine of formula (I) taken out from the reaction liquor or kept in the reaction liquor with water in the presence of an organic solvent, i.e., in the form of a solution or suspension in the organic solvent.

A particularly important feature of the present invention resides, therefore, in the use of an acid adduct salt of acetonine of formula (I) as a starting material.

Organic solvents used in the preparation of an acid adduct salt of acetonine of formula (I) are those inert to the reaction and containing substantially no water such as aromatic hydrocarbons, for example, benzene, toluene and xylene; and ketones, for example, acetone;

and alcohols, for example, methanol and ethanol or mixtures of such solvents. The reaction is carried out at a temperature kept in the range of 0° to 10°C., preferably 0° to 5°C. The acids are used in a stoichiometric amount based on acetonine. Acids used therefore may be such which form acid radicals and are especially those as defined above for HnX.

Preferred acids are mineral acids, carboxylic acids and sulfonic acids, particularly hydrohalogenic acids, sulfuric acid, nitric acid, phosphoric acid, formic acid, acetic acid, chloroacetic acid, dichloroacetic acid, trichloroacetic acid, trifuoroacetic acid, maleic acid, succinic acid, benzoic acid, cinnamic acid and aromatic and aliphatic sulfonic acids. Most preferably, hydrochloric acid, sulfuric acid, nitric acid, methanesulfonic acid, p-toluenesulfonic acid and benzenesulfonic acid are used. Most practically, gaseous hydrogen chloride, sulfuric acid and p-toluenesulfonic acid are used. The acid adduct salt of acetonine of formula (I) is generally obtained in the form of crystals precipitated in the solvent used or in the form of solution in the solvent.

The acid adduct salt of acetonine thus formed is sent to the second step after it is taken out from the reaction liquor of the first step or not taken out. The acid adduct salt of acetonine taken out is fed into the second step in the form of a solution or suspension in an organic solvent. In case the acid adduct salt of acetonine is not taken out from the solution or suspension, the reaction liquor of the first step is used directly in the second step. As organic solvent used in the second step, there may be mentioned organic solvents inert to the reaction as in the first step such as aromatic hydrocarbons, for example, benzene, toluene and xylene, ketones, for example, acetone; and alcohols, for example, methanol and ethanol. Preferred solvents are acetone and methanol. In the reaction of the acid adduct salt of acetonine and water, the reaction liquor is added with water diluted or not diluted with said organic solvents under stirring. The preferred quantity of water is stoichiometric one, namely, 1 molar equivalent based on the acid adduct salt of acetonine. If water is used in a far larger quantity, yield of the final product may be reduced. Crystal water of the starting material may also be used as the water. The reaction may be carried out e.g., at a temperature in the range of 5° to 40°C., preferably 10° to 25°C.

In the process according to the invention, preferably at least an equimolar amount of water based on acetonine is used. More favourably, the water is used in a mole ratio of acetonine to water of 1:1 up to 1:5. However, if diacetone alcohol or preferably acetone is used as solvent in the reaction, water may be used in a quantity of less than 1 molar equivalent based on acetonine. However, the reaction is not performed under anhydrous or substantially anhydrous conditions. It is especially advantageous to introduce one mole of water into the reaction in the form of acetonine hydrate. Also, water can be introduced into the reaction by using hydrates of salts.

Especially high yields are obtained by employing as catalyst a molar excess amount based on acetonine of an ammonium salt and performing the reaction in acetone as solvent.

Usually, the reaction is terminated within 1 to 20 hours, especially 2 to 10 hours.

The yields of the process according to the invention may be improved and the reaction time shortened by adding, in addition to the acid catalyst, 0.01 to 0.5 mole % based on acetonine of another catalyst selected from the group consisting of potassium iodide, sodium iodide, lithium bromide, lithium iodide, lithium thiocyanate, ammonium thiocyanate, lithium cyanide, lithium nitrate, ammonium sulfide, bromine, iodine or the bromide, iodide, nitrate, methanesulfonate, benzenesulfonate or p-toluenesulfonate of ammonia, triethylamine, urea or thiourea.

Triacetonamine is usually obtained in yields of more than 85%. Yields of even more than 100% based on acetonine can be obtained if the reaction is performed in the solvents like acetone.

After the completion of the reaction, the aimed triacetonamine is separated from the reaction solution in a usual manner, e.g., by isolation of the corresponding salts as hydrate or by distillation.

By-products of the reaction are present only in small amounts and, therefore, the purification of the final product and removal of the by-products are easy.

Thus, as compared with the conventional processes, the process of the present invention is a quite excellent process for preparing triacetonamine on a commercial scale.

The industrial value of the process is quite high, since tiracetonamine and especially its derivatives are used in a large amount as photostabilizers for polymeric materials and as starting materials for the synthesis of pharmaceuticals.

The process of the present invention is illustrated by the following examples.

EXAMPLE 1

80 ml. of Acetone was added to 34.4 g. of mono-p-toluenesulfonic acid salt of acetonine (decomposition point : 115°–117°C.) and the mixture was added dropwise with a solution of 2 ml. of water in 20 ml. of acetone under stirring at 5°–10°C. After completion of the addition, the whole was stirred at room temperature (20°–25°C.) for 8 hours to effect the reaction. Crystals mainly comprising ammonium salt of p-toluenesulfonic acid thus precipitated were filtered out. The precipitate was washed with cold acetone and the washing was combined with the filtrate and concentrated. The concentration residue was dissolved in benzene, washed with 10% aqueous potassium carbonate solution and dried over anhydrous potassium carbonate. Benzene was then distilled out. The residue was subjected to distillation under reduced pressure to obtain 14.1 g. of triacetonamine in the form of pale yellow liquid boiling at 75°–76°C./4 mmHg. Upon cooling, the liquid grew into crystals melting at 35°–36°C. Yield, 91.0%.

Analysis for $C_9H_{17}NO$: Calculated: C, 69.63%; H, 11.04%; N, 9.02%. Found: C, 69.60%; H, 11.03%; N, 9.06%.

IR Spectrum (liquid film) : $\nu_{NH} 3320 cm^{-1}$, $\nu_{C=O} 1707 cm^{-1}$

IR Spectrum and NMR spectrum of the product coincided with those of a standard.

EXAMPLE 2

60 ml. of Methanol was added to 20.3 g. of diacetonium sulfate (decomposition point : 166°–168°C.) and the mixture was added dropwise with hydrous methanol comprising 15 ml. of methanol and 2 ml. of water under stirring at 15°C. After completion of the addition, the whole was stirred at 20°–25°C. for 7 hours to effect the reaction. The reaction liquid was neutralized by addition of potassium carbonate and methanol was distilled out. The residue was extracted with benzene. The benzene solution was dried over anhydrous potassium carbonate and benzene was distilled out. The residue was subjected to distillation under reduced pressure to obtain 13.7 g. of triacetonamine in the form of pale yellow liquid boiling at 78°–79°C./ 6 mmHg. Upon cooling, the liquid grew into crystals melting at 35°–36°C. Yield, 88.3%.

IR Spectrum and NMR spectrum of the product coincided with those of a standard.

EXAMPLE 3

A solution of 19 g. of p-toluenesulfonic acid monohydrate in 40 ml. of acetone was added dropwise to a solution of 15.5 g. of acetonine in 30 ml. of acetone under cooling to 0°–5°C. and under stirring, to form p-toluenesulfonic acid salt of acetonine. The mixture was stirred at 25°C. for 10 hours to effect the reaction and cooled with ice. Crystals thus formed were filtered out and washed with cold acetone and the washing was combined with the filtrate and concentrated. The concentration residue was extracted with benzene. The benzene solution was washed with 20% aqueous sodium hydrogencarbonate solution and dried with anhydrous potassium carbonate. Benzene was then distilled out. The residue was subjected to distillation under reduced pressure to obtain 13.5 g. of triacetonamine in the form of pale yellow liquid boiling at 79°C./6 mmHg. Yield, 86.7%.

IR Spectrum and NMR spectrum of the product coincided with those of a standard.

EXAMPLE 4

A solution obtained by browing 8.4 g. of dry hydrochloric acid gas in 40 ml. of acetone was added dropwise to a solution of 30.8 g. of acetonine in 90 ml. of acetone. After completion of the addition, the whole was stirred at 5°–10°C. for 50 minutes. During the stirring, acetonine monohydrochloride was precipitated, which was isolated and confirmed by IR spectrum. Hydrous acetone comprising 4 ml. of water and 30 ml. of acetone was added thereto dropwise at the same temperature. Thereafter, the whole was stirred at a temperature of 20°–25°C. for 6 hours to effect the reaction and concentrated. The concentration residue was added with aqueous potassium carbonate solution and extracted with benzene. The benzene solution was dried over anhydrous potassium carbonate and concentrated. The concentration residue was subjected to distillation under reduced pressure to obtain 28.6 g. of triacetonamine in the form of pale yellow liquid boiling at 78°–79°C./6 mmHg. Yield, 92.3%.

IR Spectrum and NMR spectrum of the product coincided with those of a standard.

EXAMPLE 5

A mixture of 5.0 g. of acetonine hydrate, 1.7 g. of acetic acid and 40.0 g. of acetone was heated at 60°C. for 10 hours in a sealed equipment to effect the reaction. After completion of the reaction, the solvent was distilled off and the residue was added with saturated acqueous potassium carbonate solution, then extracted with benzene. The extract was dried over anhydrous potassium carbonate, then benzene was distilled off and the residue was purified by distillation under reduced pressure to give triacetonamine in a yield of 95.9%.

EXAMPLE 6

Following the substantially same procedure as shown in Example 5 except that 0.4 g. of formic acid was used in place of acetic acid, triacetonamine was obtained in a yield of 103%.

EXAMPLE 7

5.0 g. of Acetonine hydrate and 3.5 g. of benzoic acid were added to a mixture of 20.0 g. of acetone and 20.0 g. of methanol and the mixture was stirred at room temperature for 24 hours to effect the reaction. After completion of the reaction, the reaction mixture was purified in the same manner as in Example 1 to obtain triacetonamine in a yield of 90.3%.

EXAMPLE 8

15.4 g. of Acetonine was dissolved in a mixed solvent comprising 169.8 g. of acetone and 56.6 g. of methanol. The solution was ice-cooled, added with 12.9 g. of dichloroacetic acid and 1.8 g. of water under stirring. The mixture was stirred at room temperature for 24 hours to effect the reaction. After completion of the reaction, the reaction mixture was concentrated under reduced pressure, added with 40% aqueous potassium carbonate solution and extracted with ether. The extract was dried over anhydrous potassium carbonate, then ether was distilled off and the resulting residue was purified by distillation under reduced pressure to obtain triacetonamine in a yield of 136%.

EXAMPLE 9

5.0 g. of Acetonine, 0.5 g. of water and 3.1 g. of methanesulfonic acid were added to a mixed solvent comprising 35 g. of acetone and 35 g. of methanol. The mixture was stirred at room temperature for 24 hours to effect the reaction. After completion of the reaction, the reaction mixture was purified in the same manner as in Example 5 to obtain triacetonamine in a yield of 130%.

EXAMPLE 10

5.0 g. of Acetonine was dissolved in a mixed solvent comprising 10 g. of acetone and 10 g. of methanol. The solution was added dropwise with a solution of 2.1 g. of nitric acid containing 0.63 g. of water in 10 g. of acetone and 10 g. of methanol at 15°–20°C. After completion of the addition, the mixture was maintained at room temperature for 24 hours to effect the reaction. After completion of the reaction, the reaction mixture was purified in the same manner as in Example 5 to obtain triacetonamine in a yield of 119%.

EXAMPLE 11

A solution of 7.7 g. of acetonine in 15 ml. of ether was added dropwise with a solution of 8.1 g. of trichloroacetic acid in 15 ml. of ether at 5°–10°C. under stirring. After completion of the addition, the whole was stirred for 1–2 hours. Crystals thus precipitated were filtered, washed with ether and dried under reduced pressure to give 15.5 g. of acetonine trichloroacetate as colorless crystals melting at 113°–114°C. Yield, 97.9%.

EXAMPLES 12 – 20

Following the substantially same procedure as shown in Example 11, the following acetonine salts were obtained.

| No. of Example | Acetonine salt | Melting point (°C.) |
|---|---|---|
| 12 | acetonine p-tosylate | 115 – 117 |
| 13 | diacetonium sulfate | 166 – 168 |
| 14 | acetonine hydrochloride | 123 – 125 |
| 15 | acetonine dichloroacetate | 106 – 108 |
| 16 | acetonine acetate | 102 – 103 |
| 17 | acetonine formate | 66 – 68 |
| 18 | diacetonium maleate | 103 – 104 |
| 19 | acetonine benzoate | 117 – 118 |
| 20 | acetonine cinnamate | 115 – 117 |

EXAMPLE 21

A mixture of 6.2 g. of diacetonium maleate, 40.0 g. of acetone and 0.5 g. of water was heated at 60°C. for 10 hours in a sealed equipment to effect the reaction. After completion of the reaction, the reaction mixture was purified in the same manner as in Example 5 to obtain triacetonamine in a yield of 133%.

EXAMPLE 22

Following the substantially same procedure as shown in Example 21 except that 8.78 g. of acetonine cinnamate was used in place of diacetonine maleate, triacetonamine was obtained in a yield of 91.3%.

EXAMPLE 23

31.8 g. of Acetonine trichloroacetate was added to a mixed solvent comprising 190.8 g. of acetone and 63.6 g. of methanol. The mixture was added dropwise with 1.8 g. of water at room temperature under stirring. After completion of the addition, the whole was stirred at room temperature for 8 hours, then allowed to stand overnight to complete the reaction. The reaction mixture was purified in the same manner as in Example 8 to obtain triacetonamine in a yield of 166%.

EXAMPLES 24 – 29

A solution of 5.0 g. of acetonine hydrate in a mixed solvent comprising 8.5 g. of methanol and 16.9 g. of acetone was added with a catalyst listed below. The mixture was stirred at room temperature for 24 hours to effect the reaction. After completion of the reaction, the reaction mixture was purified in the same manner as in Example 5 to obtain triacetonamine in a yield as shown hereinbelow.

| No. of Example | Catalyst | Amount used (g.) | Yield of triacetonamine (%) |
|---|---|---|---|
| 24 | urea nitrate | 0.9 | 90.2 |
| 25 | thiourea hydrochloride | 3.3 | 146 |
| 26 | ammonium acetate | 2.2 | 91.8 |
| 27 | pyridine formate | 1.8 | 99.0 |
| 28 | triethylamine hydrochloride | 4.0 | 102 |
| 29 | ammonium p-toluenesulfonate | 6.0 | 171 |

EXAMPLES 30 – 31

A solution of 5.0 g. of acetonine hydrate in a mixed solvent comprising 16.9 g. of acetone and 1.7 g. of methanol was added with a catalyst listed below and the mixture was heated to 60°C. for 7 hours in a sealed equipment to effect the reaction. After completion of the reaction, the reaction mixture was purified in the same manner as in Example 5 to obtain triacetonamine in a yield as shown hereinbelow.

| No. of Example | Catalyst | Amount used (g.) | Yield of triacetonamine (%) |
|---|---|---|---|
| 30 | triethylamine p-toluenesulfonate | 4.0 | 127 |
| 31 | triacetonamine hydrochloride | 1.4 | 184* |

*Amount of triacetonamine used as catalyst is deducted.

EXAMPLE 32

A mixture of 5.0 g. of acetonine hydrate, 5.7 g. of ammonium bromide and 38.8 g. of acetone was heated at 60°C. for 10 hours to effect the reaction. After completion of the reaction, the reaction mixture was purified in the same manner as in Example 5 to obtain triacetonamine in a yield of 220%.

EXAMPLE 33

A solution of 15.4 g. of acetonine in 100 ml. of dimethylformamide was added with 19.0 g. of p-toluenesulfonic acid monohydrate. The mixture was stirred at room temperature for 8 hours, then allowed to stand overnight to complete the reaction. After completion of the reaction, the reaction mixture was added with 30% aqueous sodium hydroxide solution and extracted with ether. The extract was dried over anhydrous potassium carbonate and ether was distilled off. The resulting residue was purified by distillation under reduced pressure to obtain triacetonamine in a yield of 88.8%.

EXAMPLE 34

A solution of 5.0 g. of acetonine in 33.8 g. of methylethyl ketone was added with 6.2 g. of p-toluenesulfonic acid monohydrate under stirring. The mixture was stirred at room temperature for 8 hours to effect the reaction. After completion of the reaction, the reaction mixture was purified in the same manner as in Example 8 to obtain triacetonamine in a yield of 91.7%.

EXAMPLES 35 – 38

5.0 g. of Acetonine and 3.2 g. of ammonium bromide were heated at 44°C. for 15 hours in a mixed solvent comprising acetone and water in various ratios as shown hereinbelow to effect the reaction. After completion of the reaction, the reaction mixture was purified in the same manner as in Example 5 to obtain triacetonamine in a yield as shown hereinbelow.

| No. of Example | Mixed solvent Acetone (g.)/ | Water (g.) | Yield of triacetonamine (%) |
|---|---|---|---|
| 35 | 39.7 | 0.3 | 175 |
| 36 | 39.1 | 0.9 | 191 |
| 37 | 38.1 | 1.7 | 203 |
| 38 | 37.1 | 2.9 | 198 |

EXAMPLES 39 – 42

A mixture of 3.0 g. of acetonine hydrate, 9.0 g. of acetone and 0.60 g. of ammonium chloride as catalyst was added with another catalyst listed below. The mixture was stirred at 40°C. in a flask fitted with a stopper, and the yield of triacetonamine was determined at regular intervals. The time required to obtain triacetonamine in a yield of 90% is shown hereinbelow.

| No. of Example | Another catalyst | Amount used (g) | Time (hours) |
|---|---|---|---|
| Control | — | — | 42 |
| 39 | sodium iodide | 0.10 | 14 |
| 40 | potassium iodide | 0.12 | 12 |
| 41 | ammonium iodide | 0.10 | 11.5 |
| 42 | iodine | 0.18 | 11 |

What is claimed is:

1. A Process for preparing triacetonamine comprising reacting acetonine with water in the presence of at least 12.5 mol-% based on acetonine of an acid catalyst selected from the group consisting of a mineral acid, a carboxylic acid, an organic sulfur-oxygen-, organic phosphorus-oxygen acid, salt of said acids with ammonia or a nitrogen-containing organic base, and mixture of said acid catalysts.

2. A process according to claim 1 wherein water is used in a quantity of less than an equimolar amount based on acetonine together with acetone or diacetone alcohol.

3. A process according to claim 2, wherein water is used in a quantity of less than an equimolar amount based on acetonine together with acetone.

4. A process according to claim 1, wherein at least an equimolar amount of water based on acetonine is used.

5. A process according to claim 4, wherein the reaction is performed in the presence of an organic solvent or mixtures of organic solvents.

6. A process according to claim 5, wherein the as a solvent used the a ketone other than acetone, diacetone alcohol, mesityl oxide, diacetonamine, triacetondiamine or phorone and the reaction is performed at a temperature of from −15° to +40°C.

7. A process according to claim 5, wherein the solvent used is acetone, diacetone alcohol, mesityl oxide, diacetonamine, triacetondiamine, lower alcohols having from 1 to 4 carbon atoms, ethylene glycol monomethylether or mixtures of such solvents.

8. A process according to claim 7, wherein the lower alcohol used is methanol.

9. A process according to claim 7, wherein the solvent used is acetone.

10. A process according to claim 1, wherein the carboxylic-, organic sulfur-oxygen- or phosphorus-oxygen acids used have a pKa-value in water of below 5.

11. A process according to claim 10, wherein the organic sulfur-oxygen- acids are sulfonic acids.

12. A process according to claim 1, wherein the acid used as the acid catalyst has a pKa-value in water of 1.5 or lower.

13. A process according to claim 1, wherein the acid used as the acid catalyst is selected from the group consisting of hydrochloric acid, hydrobromic acid, hydroiodic acid, sulfuric acid, nitric acid, benzenesulfonic acid, p-toluenesulfonic acid, methanesulfonic acid, dichloroacetic acid, and trichloroacetic acid.

14. A process according to claim 1, wherein the salt used as an acid catalyst is a salt of a nitrogen-containing organic base with a mineral-, carboxylic-, organic sulfur-oxygen- or organic phosphorus-oxygen acid.

15. A process according to claim 1, wherein the salt used as an acid catalyst is an ammonium salt of a mineral-, carboxylic-, organic sulfur-oxygen- or organic phosphorus-oxygen acid.

16. A process according to claim 1, wherein the salt used as an acid catalyst is an ammonium salt of hydrochloric, hydrobromic, hydroiodic, nitric, benzenesulfonic, p-toluenesulfonic, methanesulfonic, dichloroacetic or trichloroacetic acid.

17. A process according to claim 1, wherein the salt used as an acid catalyst is a salt of one of the acids selected from the group consisting of hydrochloric, hydrobromic, hydroiodic, nitric, benzenesulfonic, p-toluenesulfonic, methanesulfonic, dichloroacetic and trichloroacetic acid with one of the bases selected from the group consisting of triacetonamine, triethylamine, urea and thiourea.

18. A process according to claim 1, wherein the mineral acid, carboxylic acid, organic sulfur-oxygen acid or organic phosphorus-oxygen acid is used in a stoichiometric ratio to the acetonine.

19. A process according to claim 18, wherein the reaction is performed by using an acid adduct salt of acetonine of the formula

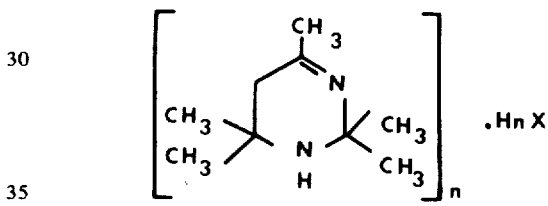

wherein HnX represents an acid as defined in claim 18 and n represents the same number as the ionic valence of the acid radical X of the acid, and reacting the salt with water in the presence of an organic solvent.

20. A process according to claim 19, wherein HnX represents a mineral acid or sulfonic acid.

21. A process according to claim 20, wherein the mineral acid or sulfonic acid is an acid selected from the group consisting of hydrohalogenic acids, sulfuric acid, nitric acid, phosphoric acid and aliphatic and aromatic sulfonic acids.

22. A process according to claim 20, wherein the mineral acid or sulfonic acid is an acid selected from the group consisting of hydrochloric acid, sulfuric acid, nitric acid, methanesulfonic acid, p-toluenesulfonic acid and benzenesulfonic acid.

23. A process according to claim 20, wherein the mineral acid is hydrochloric acid gas.

24. A process according to claim 20, wherein the mineral acid is sulfuric acid.

25. A process according to claim 20, wherein the sulfonic acid is p-toluenesulfonic acid.

26. A process according to claim 1, wherein the reaction is performed at a temperature of above −15°C.

27. A process according to claim 26, wherein the reaction temperature is from −15° to +150°C.

28. A process according to claim 26, wherein the a reaction temperature is from 0° to 110°C.

29. A process according to claim 26, wherein the a reaction temperature is from 0° to 65°C.

30. A process according to claim 4, wherein water is used in a ratio of acetonine to water of 1 : 1 up to 1 : 5.

31. A process according to claim 4, wherein 1 mol of water is introduced into the reaction in the form of acetonine hydrate.

32. A process according to claim 19, wherein water is used in a quantity of 1 molar equivalent based on the acid adduct salt of acetonine and the reaction is carried out at a temperature of 5° to 40°C.

33. A process according to claim 19, wherein acetonine is reacted with a stoichiometric amount of an acid in the presence of an organic solvent at a low temperature to form an acid adduct salt of acetonine of the formula

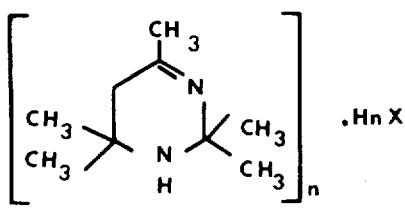

wherein HnX represents an acid as defined in claim 19 and n represents the same number as the ionic valence of acid radical X of the acid, and thus obtained acid adduct salt is reacted with water in the presence of an organic solvent.

34. A process according to claim 33, wherein the acid HnX is a mineral acid or sulfonic acid.

35. A process according to claim 33, wherein the acid HnX is a carboxylic acid.

36. A process according to claim 34, wherein the mineral acid or sulfonic acid is an acid selected from the group consisting of hydrohalogen acid, sulfuric acid, nitric acid, and aromatic sulfonic acids.

37. A process according to claim 34, wherein the mineral acid or sulfonic acid is an acid selected from the group consisting of hydrochloric acid, sulfuric acid, nitric acid, methanesulfonic acid, p-toluenesulfonic acid and benzenesulfonic acid.

38. A process according to claim 34, wherein the mineral acid is hydrochloric acid gas.

39. A process according to claim 34, wherein the mineral acid is sulfuric acid.

40. A process according to claim 34, wherein the sulfonic acid is p-toluenesulfonic acid.

41. A process according to claim 33, wherein the reaction in the first step is carried out at a temperature of 0° to 10°C. and the reaction in the second step is carried out at a temperature of 5° to 40°C. by using water in a quantity of 1 mol equivalent based on the acid adduct salt of acetonine.

42. A process according to claim 5, wherein the reaction is performed in acetone as solvent and that a molar excess amount based on acetonine of an ammonium salt is used as an acid catalyst.

43. A process according to claim 1, wherein in addition to the acid catalyst is used a different catalyst, in an amount of 0.01 to 0.5 mol-% based on acetonine.

44. A process according to claim 43, wherein said different catalyst is selected from the group consisting of potassium iodide, sodium iodide, lithium bromide, lithium iodide, lithium thiocyanate, ammonium thiocyanate, lithium cyanide, lithium nitrate, ammonium sulfide, bromine, iodine, the bromide, iodide, nitrate, methanesulfonate, benzenesulfonate or p-toluenesulfonate of ammonia, triethylamine, urea, and thiourea.

45. A process according to claim 1, wherein the nitrogen-containing organic base is triacetonamine, triethylamine, urea or thiourea.

46. A process according to claim 1, wherein the salt used as an acid catalyst is a salt of hydrochloric, hydrobromic, hydroiodic, nitric acid or an organic sulfonic or halogenoacetic acid.

* * * * *